United States Patent [19]

Helmstetter

[11] 4,055,554

[45] Oct. 25, 1977

[54] GEL STRENGTH ENHANCER FOR GELATIN COMPOSITIONS INCLUDING AN OXIDIZED POLYSACCHARIDE

[75] Inventor: Gerald J. Helmstetter, Bridgewater, N.J.

[73] Assignee: National Starch and Chemical Corporation, Bridgewater, N.J.

[21] Appl. No.: 721,954

[22] Filed: Sept. 10, 1976

[51] Int. Cl.$^2$ .............................................. C09H 7/00
[52] U.S. Cl. ...................................... 260/117; 96/111; 106/129; 106/130
[58] Field of Search ........................ 260/117; 96/111; 106/129, 130

[56] References Cited

U.S. PATENT DOCUMENTS

| | | | |
|---|---|---|---|
| 2,317,752 | 4/1943 | Fuller | 536/105 X |
| 2,461,139 | 2/1949 | Caldwell | 536/110 |
| 2,661,349 | 12/1953 | Caldwell et al. | 536/63 |
| 2,813,093 | 11/1957 | Caldwell et al. | 536/50 |
| 3,057,723 | 10/1962 | Jeffreys et al. | 96/111 X |
| 3,058,827 | 10/1962 | Graham | 260/117 X |
| 3,062,652 | 11/1962 | Jeffreys et al. | 96/111 X |
| 3,108,995 | 10/1963 | Tourtellotte et al. | 260/117 |
| 3,758,323 | 9/1973 | Szymanski et al. | 106/130 X |
| 3,865,603 | 2/1975 | Szymanski et al. | 106/130 |

*Primary Examiner*—Howard E. Schain
*Attorney, Agent, or Firm*—Edwin Szala; Ellen T. Dec

[57] ABSTRACT

Chemically modified dialdehyde polysaccharides are used as gel strength enhancers for gelatin compositions. These modified polysaccharides are particularly useful as gel strength enhancers for gelatin compositions which have been extended with starch or dextrin.

12 Claims, No Drawings

GEL STRENGTH ENHANCER FOR GELATIN COMPOSITIONS INCLUDING AN OXIDIZED POLYSACCHARIDE

BACKGROUND OF THE INVENTION

I. Field of the Invention

Chemically modified dialdehyde polysaccharides provide superior hardeners for gelatin compositions. In particular, the use of the specific dialdehyde polysaccharides disclosed herein enables replacement of gelatin with non-gelatin materials at high concentration levels with an improvement in hardening properties.

II. Brief Description of the Prior Art

The use of dialdehyde polysaccharides, particularly dialdehyde starches and gums, as hardeners for gelatin films is known in the art and may be represented by the disclosures in U.S. Pat. Nos. 3,057,723 and 3,058,827 as well as in British Pat. No. 891,221. It is also known and disclosed in U.S. Pat. Nos. 3,865,603 and 3,758,323 that gelatin may be extended with certain chemically modified fluidity or chemically modified thermally converted starches or dextrins. Although it has been found that replacement of the gelatin with the latter starches or dextrins may be made at relatively high levels while maintaining compatibility of the gelatin and starch mixture, the films resulting from such high replacement levels suffer some undesirable reduction in hardness.

For economical reasons, it is apparent that the higher levels of gelatin replacement are desirable and there is thus a need in the art for a superior hardener for gelatin compositions in general and particularly for extended gelatin compositions.

SUMMARY OF THE INVENTION

I have now found that the addition to gelatin compositions of polysaccharides which have been oxidized to an extent that 0.5 to 100 percent of the original anhydroglucose units have been converted to dialdehyde units and subsequently subjected to chemical modification under aqueous alkaline conditions with a mono-reactive reagent to a degree of substitution (D.S.) of at least 0.005, provides a synergistic improvement in gel strength and hardness when compared with the results obtained using the unmodified dialdehyde polysaccharides of the prior art. Moreover, the use of the specific chemically modified dialdehyde polysaccharides enables the satisfactory replacement of gelatin with the starches or dextrins disclosed in the U.S. Pat. Nos. 3,865,603 and 3,758,323 patents at levels of up to about 75%.

As a further aspect of the invention, the modified dialdehyde polysaccharides may be spray dried to yield a stable product which may be added to gelatin dispersions or extended gelatin dispersions without the necessity for cooking.

DETAILED DESCRIPTION OF THE PREFERRED EMBODIMENTS

The polysaccharides employed as base materials to produce the unique hardeners disclosed herein may comprise any of the conventionally employed polysaccharides containing adjacent hydroxyl groups available for reaction. The preferred and most commonly employed polysaccharides are the starch bases derived from any plant source including corn, waxy maize, potato, sweet potato, wheat, rice, sago, tapioca, sorghum, high amylose corn and the like. Other polysaccharides which are also useful herein include the naturally occurring gums such as gum acacia, gum tragacanth, guar gum, locust bean gum, cellulose, dextrans, algins, inulins, etc.

In accordance with the present invention, the polysaccharide bases are first oxidized to convert all or a portion of the original anhydroglucose units to dialdehyde units. This oxidation step is conventionally accomplished using periodic acid as described in U.S. Pat. Nos. 2,648,629; 2,713,553; 2,770,589 and 2,830,941 among others, although other methods which result in the desired conversion can be employed. The dialdehyde polysaccharides useful herein can be from 0.5 to 100 percent oxidized. In general, it is preferred to use dialdehyde polysaccharides which have been from about 90 to 100 percent oxidized; i.e., those polysaccharides wherein about 90 to 100 of each 100 of the original anhydroglucose units have been converted to dialdehyde units by periodate oxidation.

The preparation of the derivatized polysaccharides may be carried out by any conventional method whereby the available hydroxyl groups of the dialdehyde polysaccharide base are partially (or completely) modified by the mono-reactive modifying reagent. Typical methods for the preparation of modified starch derivatives are discussed by H. J. Roberts in *Starch: Chemistry and Technology*, Vols. I and II, Academic Press, New York, 1965 and 1967, respectively; various other methods would include those taught in assignee's U.S. Pat. Nos. such as 2,461,139; 2,661,349; 2,802,000; 2,813,093 and 2,825,727, all of which are fully incorporated herein by reference. Similar technology may be applied to produce chemical derivatives of other polysaccharides.

The specific modifications chosen will depend on the usefulness, availability and cost. Among the useful modifications are those which will result in the corresponding succinate, acetate, alkenyl succinate, diethylaminoethyl ether, phthalate, sulfonate, carboxymethylated hydroxypropylated and chlorinated derivatives of the polysaccharide base. Preferred modifications for the polysaccharides are the octenyl succinated types.

The order in which the two reactions are carried out has been found to be critical to achieving satisfactory hardening in accordance with the method of the present invention. It is essential that the starch be subjected to the dialdehyde treatment prior to the derivatization. Thus, the etherified dialdehyde polysaccharides which are first derivatized and then treated with periodate and which are disclosed in U.S. Pat. No. 3,087,852 and taught to be useful in making wet strength paper are not useful in the present invention.

The "gelatins" which may be hardened using the modified dialdehyde polysaccharides disclosed herein include any proteinaceous materials derived by hydrolytic extraction of collagen obtained from the bones, skins and connective tissues of animals. Such materials may be obtained by hydrolytic extraction in an alkaline (lime) or acidic medium and thereafter treated for use in a particular industry. For example, the gelatin may be produced by accurately controlling the depolymerization of the protein collagen and then chemically refining, e.g., by ion exchange, to meet the specifications appropriate for use in a particular industry.

If the modified dialdehyde polysaccharides are to be used as hardeners for extended gelatin compositions, the gelatin extender may be present in an amount of up to about 75% by weight of the total solids and should be one of the modified starches or dextrins disclosed in assignee's U.S. Pat. Nos. 3,865,603 and 3,758,323 respectively, the disclosures of which are fully incorporated herein by reference.

Thus, modified starches useful as extenders herein comprise either the chemically modified fluidity starches or the chemically modified, thermally converted starches having a degree of substitution of at least 0.008. The modified starches are selected from the group consisting of the succinates, alkenyl succinates, diethylaminoethyl ethers, phthalates, sulfonates, carboxymethylated and chlorinated derivatives, and being chosen so that an aqueous dispersion containing 30 percent, by weight, total solids comprising the chosen proportions of said modified starch and gelatin held at a temperature of 58° C. for 16 hours exhibits no phase separation.

Similarly, the particular dextrin chosen as a gelatin extender must be chosen so that an aqueous dispersion containing 30 percent, by weight, total solids comprising the chosen proportions of dextrin and gelatin, held at a temperature of 58° C. for 16 hours exhibits no phase separation.

It has been found that when the hardeners described herein are used for extended gelatin compositions, the dextrin or modified starch extenders may be present in amounts of up to 75% by weight total solids and still result in the production of a satisfactory film. When compared with the hardness properties obtained using gelatin alone (with no hardener), superior gel strength and hardness properties will be obtained at levels of extender up to and exceeding 50% by weight total solids, with about comparable results obtained at a 60% extender level. Above about 60% replacement, hardness properties will diminish but replacement may be increased to about 75% without unacceptable loss in properties.

The amount of modified dialdehyde polysaccharide employed as hardener will vary depending upon the level of treatment (both dialdehyde and modifications) on the polysaccharide, the degree of hardness required, the solids concentration of the system, the absence or presence of starch or dextrin extenders, etc. Thus, the use of even trace amounts of the modified dialdehyde polysaccharides will result in improvement in the hardness of the films, however, generally amounts of at least about 0.5% based on total solids weight, are employed with gelatins in which there are no extenders present and amounts of at least about 1%, by weight solids, employed in extended gelatin compositions. Amounts greater than about 5 and 10%, by weight solids, for the unextended and extended gelatin compositions, respectively, are usually not required and their presence will contribute no advantage to the hardening of the films.

The hardeners may be used by merely mixing the dry components and placing the dry mix in aqueous dispersion or by mixing the modified dialdehyde polysaccharide into an aqueous gelatin or extended gelatin dispersion. In the case of extended gelatin compositions it is usually most convenient to blend the appropriate proportions of two starches or the starch and dextrin components and add this dry blend to the gelatin. The hardeners may also be incorporated into such compositions in which inorganic materials are also present such as silver halide photographic emulsions, silver halide photographic emulsion containing incorporated color-forming couplers, barium sulfate suspensions in aqueous gelatin or suspensions of titanium dioxide in which gelatin is the protective colloid. The hardening agents described herein are particularly useful in photographic emulsions, photographic coatings and carriers in the preparation of pharmaceutical capsules and industrial coatings.

The films obtained from the above described mixtures may be made by any conventional method designed to deposit a continuous coating or layer of the solution onto a substrate or mold of any form. Among the various techniques of coating are included spraying, dipping, air knife, trailing blade, reverse and direct roll coaters, etc. A film such as an overcoating or capsule shell may then be formed by drying the coating dispersion to a desired moisture content, using any means suitable for the particular purpose. Suitable conventional means are air, warm or cold air impingement, low humidity chamber or oven drying, etc.

If desired, the modified dialdehyde polysaccharide may be formed into a slurry, preferably with heating, and dried preferably by spray drying, to form a finely divided solidified product which will readily disperse in aqueous solutions without the necessity for cooking.

The invention will be further illustrated by, but not intended to be limited to, the following examples. In the examples all parts are by weight unless otherwise indicated.

EXAMPLE I

Dialdehyde starch approximately 90% oxidized prepared from waxy maize starch was treated with 3% by weight octenyl succinic anhydride using the basic procedure described in Example V of U.S. Pat. No. 2,661,349.

Then 9.9 parts of gelatin was hydrated in 90 parts of water and sufficient octenyl succinated dialdehyde starch added as a 10% solution to the hydrated gelatin to provide an amount of 0.1 part of the modified dialdehyde starch. The mixture was heated at 58° C. for a period of 1 hour. The resulting dispersion was poured into small jars and aged for 16 hours at 24° C., 55% relative humidity.

The strength of the gel was determined by measuring the force needed to break the surface of the gel using the plunger of a bloom gelometer fitted onto a Instron Strength Testing Machine (model T.T.C.).

As a comparison, a series of controls were also prepared and similarly tested. Thus, one control was prepared using gelatin alone, another using gelatin with the dialdehyde waxy starch and a third using dialdehyde waxy maize starch which had been further treated with alkali using the basic method disclosed in U.S. Pat. No. 3,058,827.

The results obtained are shown in Table I.

Table I

| Sample | Gel Strength |
| --- | --- |
| Dialdehyde waxy maize treated with 3% octenyl succinic anhydride and gelatin | 4.6 psi |
| Gelatin alone | 2.1 psi |
| Dialdehyde waxy maize and gelatin | 2.9 psi |
| Dialdehyde waxy maize treated with alkali and gelatin | 2.6 psi |

The results clearly show the superior gel strength obtained using the octenyl succinated dialdehyde starch in accordance with the method of the present invention.

The procedure was repeated using an octenyl succinated derivative of Sumstar 190 (a commercially available Miles Laboratories' corn starch in which 90% of the anhydroglucose units are oxidized to dialdehyde units). Similar hardening properties were observed.

EXAMPLE II

The octenyl succinated dialdehyde starch used in Example I was mixed in a ratio of 1:9 with a gelatin compatible starch, specifically the thermally modified n-octenyl succinate derivative of waxy maize starch described in Example I of U.S. Pat. No. 3,865,603.

Fifty parts of the resultant mixture were mixed with 50 parts of gelatin and hydrated for 1 hour at 58° C. and then tested as in Example I. Total solids concentration was 10% by weight.

Two control samples were also prepared, one sample containing gelatin alone and another containing the gelatin and compatible starch but lacking the hardener disclosed herein.

The results are shown in Table II.

Table II

| Sample | Gel Strength |
|---|---|
| 50 gelatin : 45 compatible starch : 5 modified dialdehyde starch hardener | 3.0 psi |
| 50 gelatin : 50 compatible starch | 1.1 psi |
| gelatin alone | 2.4 psi |

The data show that without the dialdehyde starch hardener, more than 50% of the gel strength is lost when the gelatin is extended with a compatible starch. Moreover, when the modified dialdehyde hardener is employed, there is a 20% improvement in hardness over the pure gelatin sample.

The procedure was repeated using waxy maize starches which had been 50% and 75% oxidized and then treated with 3% octenyl succinic anhydride. While the addition of the 50% oxidized starch hardener improved the gel strength of the extended gelatin compositions, the strength remained below the gel strength of a 100% gelatin dispersion. The addition of the modified 75% oxidized starch resulted in gel strength measurements equal to and exceeding that of the 100% gelatin control.

EXAMPLE III

Dialdehyde waxy maize starch was treated with 5% propylene oxide, for 16 hours at 40° C. under alkaline conditions at a pH of about 11 adjusted by periodic addition of NaOH. The resulting product was alcohol precipitated, washed and dried.

Ten parts of this starch were mixed with 90 parts of a gelatin compatible starch of the type described in Example II and cooked to obtain a complete dispersion. 50 Parts of gelatin with a bloom of 275 were mixed with 50 parts of this starch mixture on a dry solids basis and hydrated for 1 hour at 58° C. at a 10% solids concentration. Samples were tested for gel strength relative to control samples as per Example II and the results tabulated in Table III.

Table III

| Sample | Gel Strength |
|---|---|
| gelatin alone | 2.4 psi |
| 50 gelatin : 50 compatible starch | 0.7 psi |
| 50 gelatin : 45 compatible starch : 5 hydroxy- propylated dialdehyde starch hardener | 2.7 psi |

The results show that this hydroxypropylated dialdehyde waxy maize starch is also a superior hardener for extended gelatins.

EXAMPLES IV-VIII

These examples show the use of additional chemically and modified dialdehyde starches as hardeners in accordance with the present invention.

In the preparation of each of the samples the procedure of Example II was repeated, except that in each instance a different modified dialdehyde starch was substituted for the octenyl succinated dialdehyde starch used therein.

IV. A starch ester was prepared by treating waxy maize starch which had been 90% converted to dialdehyde with 3% phthalic anhydride according to the method taught in Example 7 of U.S. Pat. No. 2,461,139. The D.S. was approximately 0.024.

V. A starch ether was prepared by reacting 90% dialdehyde converted waxy maize starch with 3% beta-chlorodiethylaminoethyl chloride hydrochloride according to the method taught in Example I of U.S. Pat. No. 2,813,093. The D.S. was approximately 0.02.

VI. A starch ester was prepared by treating 90% dialdehyde converted waxy maize starch with 5% acetic anhydride according to the method taught in Example I of U.S. Pat. No. 2,451,139. The D.S. was approximately 0.06.

VII. The procedure of Example 8 of U.S. Pat. No. 2,461,139 was followed to treat 90% dialdehyde converted waxy maize starch with 3% succinic anhydride. The D.S. was approximately 0.03.

VIII. A starch was prepared by treating 90% dialdehyde converted waxy maize starch with sodium hypochlorite (3% chlorine) according to the method taught in U.S. Pat. No. 2,317,752. (approximately 0.7% COOH.)

In all examples, the addition of the modified dialdehyde starch to the extended gelatin mixture resulted in a film characterized by superior gel strength.

EXAMPLE IX

This example illustrates the criticality of the order of the two starch treatments to the successful use of the starches in the present invention.

A 3% octenyl succinated waxy maize starch was treated with periodate to a level of 97% oxidation.

The resulting dialdehyde treated esterified starch was combined with the gelatin compatible starch used in Example II and tested as described therein.

In accordance with the present invention, blends of the gelatin compatible starch and a waxy maize starch oxidized with periodic acid to a dialdehyde conversion level of 97% and then esterified with 3% octenyl succinic anhydride in accordance with the present invention were also prepared and tested. Controls using gelatin alone and extended gelatin compositions containing no hardener were also prepared and tested.

The results are shown in Table IV.

Table IV

| Blend | | Starch Amount | Gelatin Amount | Gel Strength |
|---|---|---|---|---|
| I. | (90:10) compatible starch: octenyl succinated waxy maize treated with periodate | 40 | 60 | 1.1 psi |
|  |  | 50 | 50 | 0.8 psi |
| II. | (90:10) compatible starch: dialdehyde waxy maize treated with octenyl succinic anhydride | 40 | 60 | 2.0 psi |
|  |  | 50 | 50 | 2.2 psi |
| III. | Control (gelatin alone) | 0 | 100 | 2.2 psi |
|  | Control (gelatin and compatible starch) | 40 | 60 | 1.0 psi |
|  |  | 50 | 50 | 0.5 psi |

The results clearly show the benefits with respect to gel strength of using the starch-gelatin blends designated Group II, i.e., those described in the present invention.

EXAMPLE X

This example illustrates the use as a gel strength enhancer of the modified dialdehyde starch which has been spray dried.

Thus, the procedure of Example I was repeated to produce a dialdehyde waxy maize starch which had been treated with 3% by weight octenyl succinic anhydride. The resulting modified dialdehyde starch in the form of a 10% by weight solids dispersion (pH 5.5-6.0) was passed through a spray drier having an inlet temperature of 190°-200° C. and an outlet temperature of 80°-90° C. The spray dried modified dialdehyde starch was then blended with the thermally modified n-octenyl succinate derivative of waxy maize starch in a ratio of 1:9 as described in Example II. When added to a gelatin at a level of 40% starch blend and 60% gelatin, the gel strength was found to be 2.8 psi. as compared with 1.8 psi. for a control containing only gelatin.

As will be recognized by those skilled in the art, the foregoing examples are merely exemplary. Variations may be made in ingredients, proportions and procedures as long as such variations are within the scope and spirit of the following claims.

I claim:

1. A method of hardening gelatin which comprises the step of adding to the gelatin a polysaccharide which has been oxidized to an extent that 0.5 to 100% of the original anhydroglucose units have been converted to dialdehyde units and subsequently subjected to chemical modification under aqueous alkaline conditions with a mono-reactive reagent to a degree of substitution of at least 0.005 wherein the chemical modification is one which results in a polysaccharide derivative selected from the group consisting of succinate, acetate, alkenyl succinate, diethylaminoethyl ether, phthalate, sulfonate, carboxymethylated and chlorinated derivatives.

2. The method of claim 1 wherein the polysaccharide is starch.

3. The method of claim 1 wherein 90 to 100% of the original anhydroglucose units of the polysaccharide are converted to dialdehyde units.

4. The method of claim 1 wherein the oxidation of the polysaccharide is accomplished with periodic acid.

5. The method of claim 1 wherein the chemical modification results in the octenyl succinated polysaccharide derivative.

6. The method of claim 1 wherein the chemically modified dialdehyde polysaccharide is present in an amount of 0.5 to 5% by weight of the gelatin.

7. The method of claim 1 wherein the gelatin is extended with up to 75% by weight of the total solids of a modified starch selected from the group consisting of:
   a. fluidity starches chemically modified with mono-reactive moieties having a degree of substitution at least 0.008, and
   b. thermally modified starches chemically modified with mono-reactive moieties to a degree of substitution of at least 0.008; said modified starches selected from the group consisting of the succinates, alkenyl succinates, diethylaminoethyl ethers, phthalates, sulfonates, carboxymethylated and chlorinated derivatives, and being chosen so that an aqueous solution containing 30 percent, by weight total solids comprising the chosen proportions of said modified starch extender and gelatin, held at a temperature of 58° C. for 16 hours exhibits no phase separation.

8. The method of claim 7 wherein the modified starch extender is present in an amount of less than 60% by weight of the total solids.

9. The method of claim 7 wherein the chemically modified dialdehyde polysaccharide is present in an amount of 1 to 10% by weight of the total solids.

10. The method of claim 1 wherein the gelatin is extended with up to 75% by weight total solids of a dextrin chosen so that an aqueous solution containing 30 percent, by weight, total solids comprising the chosen proportions of dextrin and gelatin, held at a temperature of 58° C. for 16 hours exhibits no phase separation.

11. The method of claim 10, wherein the dextrin is present in an amount of less than 60% by weight total solids.

12. The method of claim 10 wherein the chemically modified dialdehyde polysaccharide is present in an amount of 1 to 10% by weight of the total solids.

* * * * *